United States Patent
Lenker et al.

(10) Patent No.: US 6,176,875 B1
(45) Date of Patent: *Jan. 23, 2001

(54) LIMITED EXPANSION ENDOLUMINAL PROSTHESES AND METHODS FOR THEIR USE

(75) Inventors: Jay A. Lenker, Los Altos Hills; Brian J. Cox, Los Altos; Michael A. Evans, Palo Alto, all of CA (US); Steven Weinberg, League City, TX (US)

(73) Assignee: Medtronic, Inc., Minneapolis, MN (US)

( * ) Notice: Under 35 U.S.C. 154(b), the term of this patent shall be extended for 0 days.

This patent is subject to a terminal disclaimer.

(21) Appl. No.: 09/030,719

(22) Filed: Feb. 25, 1998

Related U.S. Application Data

(60) Division of application No. 08/595,944, filed on Feb. 6, 1996, now Pat. No. 5,843,158, which is a continuation-in-part of application No. 08/583,814, filed on Jan. 5, 1996
(60) Provisional application No. 60/019,483, filed on Jun. 10, 1996.

(51) Int. Cl.⁷ ........................................... A61F 2/06
(52) U.S. Cl. ........................................ 623/1.49; 623/1.51
(58) Field of Search .................. 623/1.49, 1.51, 623/1.15, 1.54, 1.53; 606/198

(56) References Cited

U.S. PATENT DOCUMENTS

| | | | |
|---|---|---|---|
| 3,304,557 | 2/1967 | Polansky | 3/1 |
| 3,316,557 | 5/1967 | Liebig | 3/1 |
| 3,945,052 | 3/1976 | Liebig | 3/1 |
| 4,299,015 | 11/1981 | Marcus et al. | 28/221 |
| 4,652,263 | 3/1987 | Herweck et al. | 623/1 |
| 4,731,073 | 3/1988 | Robinson | 623/1 |
| 4,834,755 * | 5/1989 | Silvestrini et al. | 623/1.49 |
| 4,922,905 | 5/1990 | Strecker | 606/195 |
| 5,037,377 | 8/1991 | Alonso | 600/36 |
| 5,064,435 * | 11/1991 | Porter | 623/1.49 |
| 5,084,065 | 1/1992 | Weldon et al. | 623/1 |
| 5,123,917 | 6/1992 | Lee | 623/1 |

(List continued on next page.)

FOREIGN PATENT DOCUMENTS

| | | | |
|---|---|---|---|
| 0 122 744 A1 | 10/1984 | (EP) | A61F/1/00 |
| 0 501 890 A1 | 9/1992 | (EP) | A61F/2/06 |
| 0 684 022 A2 | 11/1995 | (EP) | A61F/2/06 |
| 0 689 805 A2 | 1/1996 | (EP) | A61F/2/06 |
| 0 689 806 A2 | 1/1996 | (EP) | A61F/2/06 |

(List continued on next page.)

OTHER PUBLICATIONS

World Medical Manufacturing Corporation Internet WEB Page Information, downloaded Aug. 4, 1997.

*Primary Examiner*—David H. Willse
*Assistant Examiner*—Suzette J. Jackson
(74) *Attorney, Agent, or Firm*—Sterne, Kessler, Goldstein & Fox PLLC

(57) ABSTRACT

The present invention provides controlled expansion endoluminal prostheses and methods for their deployment and expansion. The present stent-grafts generally comprise a radially expansible tubular frame and a plastically expansible liner on the frame. Either the frame or the liner includes a reinforcing element which limits expansion of the stent-graft at a predetermined expanded size. In some embodiments, the reinforcing element restrains the frame, for example, by limiting the circumferential diagonals of perforations on a perforate frame structure. Generally, however, the reinforcing element is included in the liner as circumferentially oriented yarn. A particularly advantageous liner includes composite circumferential yarns having inexpansible fibers wrapped around an expansible fiber, such as a partially oriented yarn, PTFE, or the like.

9 Claims, 10 Drawing Sheets

U.S. PATENT DOCUMENTS

| | | | |
|---|---|---|---|
| 5,133,742 | 7/1992 | Pinchuk | 623/1 |
| 5,163,952 | 11/1992 | Froix | 623/1 |
| 5,282,847 | 2/1994 | Trescony et al. | 623/1 |
| 5,330,500 * | 7/1994 | Song | 623/1.49 |
| 5,387,621 | 2/1995 | Soldani | 521/155 |
| 5,413,598 * | 5/1995 | Moreland | 623/1 |
| 5,443,499 | 8/1995 | Schmitt | 623/1 |
| 5,443,500 | 8/1995 | Sigwart | 623/1 |
| 5,456,713 | 10/1995 | Chuter | 623/1 |
| 5,476,507 | 12/1995 | Wakabayashi et al. | 623/1 |
| 5,496,364 | 3/1996 | Schmitt | 623/1 |
| 5,507,770 | 4/1996 | Turk | 606/198 |
| 5,527,353 | 6/1996 | Schmitt | 623/1 |
| 5,545,209 | 8/1996 | Roberts et al. | 623/1 |
| 5,545,210 | 8/1996 | Hess et al. | 623/1 |
| 5,556,413 | 9/1996 | Lam | 606/198 |
| 5,556,426 | 9/1996 | Popadiuk et al. | 623/1 |
| 5,562,725 | 10/1996 | Schmitt et al. | 623/1 |
| 5,562,727 | 10/1996 | Truck et al. | 623/1 |
| 5,591,195 | 1/1997 | Taheri et al. | 606/194 |
| 5,591,199 | 1/1997 | Porter et al. | 606/198 |
| 5,609,605 | 3/1997 | Marshall et al. | 606/191 |
| 5,617,878 | 4/1997 | Taheri | 128/898 |
| 5,843,158 * | 12/1998 | Lenker et al. | 623/1.49 |
| 6,019,786 * | 2/2000 | Thompson | 623/1.49 |

FOREIGN PATENT DOCUMENTS

| | | | |
|---|---|---|---|
| WO 80/01460 | 7/1980 | (WO) | A61M/25/00 |
| WO 88/00813 | 2/1988 | (WO) | A61F/2/06 |
| WO 94/15548 | 7/1994 | (WO) | A61F/2/04 |
| WO 95/29647 | 11/1995 | (WO) | A61F/2/06 |
| WO 95/33422 | 12/1995 | (WO) | A61F/2/06 |
| WO 95/34255 | 12/1995 | (WO) | A61F/2/06 |
| WO 96/00103 | 1/1996 | (WO) | A61M/29/00 |
| Wo 96/10967 | 4/1996 | (WO) | A61F/2/04 |

* cited by examiner

LIMITED EXPANSION ENDOLUMINAL PROSTHESES AND METHODS FOR THEIR USE

This application is a divisional of and claims the benefit of priority form U.S. patent application Ser. No. 08/595,944, filed Feb. 6, 199, now U.S. Pat. No. 5,843,158 which is a continuation-in-part of U.S. patent application Ser. No. 08/583,814, field Jan. 6, 1996, and also claims the benefit of priority from U.S. Provisional Ser. No. 60/019,483, filed Jun. 10, 1996, and International Application Ser. No. 97/00137, field Jan. 3, 1997, the full disclosures of which are incorporated herein by reference.

BACKGROUND OF THE INVENTION

1. Field of the Invention

The present invention relates generally to tubular prostheses, such as grafts, stents, stent-grafts, and the like. More particularly, the present invention provides radially expansible tubular prosthesis structures which can be expanded up to predetermined limits to match individual body lumens, including blood vessels, particularly for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, lost occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and will equipped surgical facilities. Even with the best surgeons and equipment, however, patients being treated frequently art elderly and weakened from cardiovascular and other diseases, reducing the number of eligible patients. Even for eligible patients prior to rupture, conventional aneurysm repair has a relatively high mortality rate, usually from 2% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In Order to overcome some or all of these drawbacks, endovascular prosthesis placement for the treatment of aneurysms has been proposed. Although very promising, many of the proposed methods and apparatus suffer from undesirable limitations. In particular, proper sizing of endovascular prostheses can be problematic.

Proper matching of the prosthesis to the blood vessel is critical to the treatment of an aneurysm. The prosthesis preferably extends axially beyond the weakened portion of the blood vessel to anchor securely in the healthy vessel wall. However, the cross-sectional size and axial length of individual blood vessels vary considerably between patients. Even within a patient, the cross-section and resilience of a lumen wall can vary considerably along its axial length, and the location and extent of the aneurysm will differ with different patients. Additionally, each prosthesis must be carefully constructed and handled, making it extremely costly to provide and maintain the large selection of prostheses required for proper fitting of every individual patient.

Known radially expandable intraluminal prostheses may generally be characterized as either resilient or plastically expanded structures. Resilient intraluminal prostheses are often formed as stent-grafts having self-expanding frames or "stents" which radially conform to variations in lumenal cross-sections. Such resilient stent-grafts must expand against the luminal wall with sufficient force to anchor the prosthesis within the body lumen, and should ideally be sealed around the perimeter of the luminal wall to prevent leakage. Resilient prostheses which are too small may not expand sufficiently to seal or anchor properly, while oversized resilient prostheses can exert excessive pressure against the surrounding body lumen. Plastically expandable intraluminal prostheses have malleable frames which are expanded to fit the lumen when implanted, but the expanded prosthesis generally takes the cylindrical shape of the expanding balloon catheter, rather than conforming to irregular luminal cross-sections. Additionally, the expanded prostheses must be sufficiently large and rigid to provide a stable anchor and perimeter seal, requiring distension of the lumen adjacent the disease condition. Hence, even with proper fitting, most resilient or plastically expandable prostheses impose some stress on the body lumen. A still further complication arises from the use of a separate liner or "graft," which is often woven from inexpansible polyesters such as Dacron™, and which may therefore wrinkle and occlude the lumen if the stent graft is not fully expanded.

It has previously been proposed to use radially expansible liners with plastically expansible stents so that the liner and the frame may be expanded together within a body lumen. In particular, liner materials having undrawn or partially drawn yarns in the circumferential direction allow concurrent plastic expansion of the liner and frame using a balloon catheter. Such liner materials would thus facilitate in situ expansion of plastically expandable stent-grafts within a wide range of sizes. Unfortunately, because of the great expansibility of partially drawn yarns, any bulges formed by uneven expansion of the liner material may continue to expand in an uncontrolled manner during deployment or size adjustment. Such bulges in the liner may even result in a weak, oversized region that could potentially collect thrombus or even fail during deployment—effectively resulting in an aneurysm of the prosthesis. Furthermore, such bulges in an endoluminal prosthesis may cause folds of the liner material, leading to leakage between the prosthesis and the vessel wall.

Known prostheses having plastically expansible liner materials may suffer from additional disadvantages. As described above, such prostheses generally also include frames which are rigid hen expanded, typically relying on distension of the body lumen around a cylindrical frame to anchor and seal the prosthesis. Furthermore, undrawn or partially drawn liners may be inadvertently overexpanded, resulting in "creeping" of the material, changes in porosity, or even the creation of open fistulas. Any such overexpansion of the liner might well go undetected, as in situ expansion is generally a fluoroscopically directed process in which the condition of the liner is not easily monitored.

In co-pending U.S. patent application Ser. No. 08/538,706 (Attorney Docket No. 16380-38), which is assigned to the assignee of the present application, the full disclosure of which is incorporated herein by reference, describes a resiliently expandable prosthesis which includes a plastically expansible liner with a resilient frame, in which the resilient expansion of the frame is restrained by the liner. Advantageously, such a liner-restrained structure allows in situ expansion of the liner to match the perimeter of the surrounding body lumen, and also allows the fitted prosthesis to resiliently conform to irregular lumenal cross-sections. Application Ser. No. 08/538,706 also teaches the selective expansion of "sealing cuffs," integral or separate prosthetic end seals, which preferably include expansible liner materials to facilitate sealing and conforming an end of a tubular prosthesis against the surrounding body lumen wall. The use of liner materials with partially oriented yarns was suggested for these liner-restrained prostheses and sealing cuffs.

Although the liner-restrained prostheses, sealing cuffs, and partially drawn yarns described above provide substantial advantages over other endoluminal prosthetic structures, still further refinements are desirable. In general, it would be desirable to provide improved prostheses, including grafts and stent-grafts, and improved methods for placement of such prostheses to treat aneurysms and other conditions. It would be particularly desirable to provide liner materials for use in liner-restrained and other endoluminal prosthetic structures which would allow the prosthesis to expand plastically within a preset range, but which would reduce the danger of overexpansion. It would further be advantageous to provide liner materials which would allow controlled, selective expansion of portions of the prosthesis to promote anchoring or sealing, but which would resist expansion in alternative portions, particularly adjacent a weakened portion of a body lumen.

2. Description of the Background Art

U.S. Pat. No. 5,443,499 describes a radially expandable tubular prosthesis formed with radial yarns which are at most partially drawn. The prosthesis may optionally be secured to a bony lumen through simultaneous balloon expansion of the prosthesis and an attached stent. French Patent Application Publication No. FR 2,714,816 describes a vascular prosthesis including a sleeve which contracts axially when stretch ed radially. Sliding connections are provided between a support structure and the sleeve, and additional material is preferably provided to compensate for axial contraction of the sleeve. Similarly, U.S. Pat. No. 5,064,435 describes a self expanding prosthesis which maintains a stable axial length during expansion, by anchoring of radially outward flares at each end, and by sliding of an overlapping medial region therebetween. U.S. Pat. No. 4,834,755 describes a triaxially-braided fabric prosthesis structure to provide controlled strength and elasticity. U.S. Pat. No. 5,456,713 is generally relevant.

U.S. Pat. No. 5,258,042 describes an intravascular hydrogel implant which expands when hydrated. U.S. Pat. No. 5,470,313 describes a variable diameter balloon dilation catheter having a pressure controlled inflation profile.

SUMMARY OF THE INVENTION

The present invention provides radially expansible tubular prostheses, particularly grafts, stents, and stent-grafts, for the treatment of aneurysms, stenoses, and other disease conditions. The expansible prostheses of the present invention may be tailored by selective mechanical expansion of limited regions of the prosthesis, or may alternatively be uniformly radially expanded, depending upon the specific Requirements of the patient. Advantageously, in situ expansion is generally limited by an element of the prosthesis, e.g., by inelastic circumferential fibers of a prosthetic liner, or by a circumferential element of the frame which limits expansion, so as to avoid overexpansion of a portion of the liner. Such a self-limiting expansible structure will thus minimize the possibility of overexpanding the prosthetic lumen.

The controlled expansion of the present prostheses is generally limited by a structural element of the prosthesis itself. Hence, a stent-graft according to the invention will freely expand, either resiliently or plastically, only to some predetermined expansion limit, at which limit an element of either the liner or the frame (or both) impedes further expansion. In some cases, the expansion limit will be present in or provided on the interface between the liner and the frame, for example, a circumferential band of suture or other material which both limits stent-graft expansion and connects the liner to the frame.

The expansion limit itself may provide either a fixed radial limit or an intermediate limit. A fixed limit prevents any Significant expansion of the prosthesis beyond a maximum safe distention cross-section for the body lumen, regardless of the expansive radial force applied to the prosthesis. Such a fixed limit may also help to prevent local or global porosity of the liner from exceeding a desired maximum, to avoid the creation of fistulas, and to promote even expansion of the prosthesis, rather than bulging of any weak regions. Intermediate expansion limits will provide some mechanism which allows expansion to continue beyond an initial limit, for example, by incorporating a frangible or plastic reinforcing element in the frame or liner which fails or plastically deforms under a threshold expansive force. Intermediate limits thereby provide the safety of an expansion limitation, but with the added option of continued expansion when justified. Optionally, a plurality of intermediate limitations may Be used in series, or in combination with a fixed limit.

In a first aspect, the present invention provides a controlled expansion endoluminal stent-graft comprising a radially expansible tubular frame and a plastically expansible liner on the frame. Either the frame or the liner includes a reinforcing element which limits expansion of the stent-graft at a predetermined expanded size. Generally, the reinforcing element is included in the liner as circumferentially oriented yarn. A particularly advantageous reinforced liner includes composite circumferential yarns having inexpansible fibers wrapped around an expansible fiber, such as a partially oriented fiber, PTFE, or the like. In other embodiments, the reinforcing element restrains the frame, for example, by limiting the expansion of individual perforations on a perforate frame structure.

As used herein, "expansible" generally refers to both self-expanding structures which increase in dimensions when released from compression or subjected to a change of state (e.g., shape recovery of shape memory alloys), and also to structures which deform plastically when subjected to expansive stress. Hence, both resilient and plastically expansible (sometimes called malleable) stents are encompassed by the term "expansible frames." In contrast, "plastically expansible" herein more specifically refers to structures which plastically increases in dimension when under an expansive force.

In another aspect, the present invention provides an expansible liner stent-graft comprising a radially expansible tubular frame and a plastically expansible liner on the frame. In contrast to known expansible liner materials, the liner here comprises a fill element including fully drawn fiber which defines a maximum expanded perimeter of the liner. The fully drawn fiber may optionally wind around another fiber so as to straighten during expansion, or may alternatively be texturized or annealed after it is drawn. Advantageously, such fibers will substantially retain the ultimate strength of the fully drawn fiber.

As used herein, a "fill element" means fiber, monofilament, fiber within a thread, fiber within a yarn, a thread within a yarn, or, alternatively, a yarn itself, which forms a circumferentially oriented element of the liner material.

In another aspect, the present invention provides a limited expansion graft comprising a fabric which includes composite yarns. The composite yarns include both serpentine inexpansible fiber and expansible fiber so that the inexpansible fiber straightens when the graft is intentionally expanded. The straightening inexpansible fiber gradually becomes taut, thereby preventing expansion of the graft beyond a predetermined limit. Preferably, the inexpansible fiber is wound over the expansible fiber. Advantageously, the expansible fiber or "core" generally maintains structural integrity of the liner to prevent inadvertent deformation or distention of the prosthesis under the stresses of ordinary use.

The present invention also provides a method for deploying an endoluminal prosthesis at a target site within a diseased body lumen, the method comprising positioning the prosthesis at the target site, at which a liner of the prosthesis is plastically expanded. Advantageously, the plastic expansion of the liner is limited to a predetermined size by an element of the prosthesis.

In another aspect, the present invention provides a method for deploying an endoluminal prosthesis at a target site within a diseased body lumen, the method comprising introducing the prosthesis into the body lumen and positioning the prosthesis at the target site. A phase of a reinforcement element of the prosthesis is altered at the target site to increase expansibility of the element, and the cross-section of the prosthesis is expanded while the phase remains altered. The phase of the reinforcement element is then returned to reduce expansibility. Generally, the phase altering step comprises changing a temperature of a temperature sensitive polymer, which is ideally included in a circumferentially oriented fiber And woven into a prosthesis liner.

In another aspect, the present invention provides a method for producing a radially expansible graft, the method comprising drawing fiber to a fully drawn length and then texturizing the drawn fiber. The texturized fiber may then be woven into a tube so that the fiber is circumferentially oriented.

In yet another aspect, the present invention provides a method for producing a radially expansible graft, the method comprising drawing fiber to a fully drawn length and annealing the drawn fiber. The fiber is preferably woven into a tube so that the fiber is circumferentially oriented.

In yet, another aspect, the present invention provides a cuffed endoluminal stent-graft comprising a radially expansible tubular frame and a liner disposed on an inner or outer surface of the frame. Expansion of the stent-graft along the liner is limited to a predetermined expanded cross-section. A sealing cuff is disposed adjacent to the liner end to extend radially beyond the liner and seal between the liner and a surrounding body lumen.

In a final aspect, the present invention provides a sealing device for use with an endoluminal prosthesis, said sealing device comprising a fabric having partially oriented yarn so that the fabric is plastically expansible to seal between the prosthesis and a surrounding body lumen.

DESCRIPTION OF THE SPECIFIC EMBODIMENTS

The present invention provides controllably radially expansible tubular prostheses, particularly grafts, stents, and stent-grafts, methods for their production, and methods and devices for their deployment. The prostheses of the present invention are suitable for a wide variety of therapeutic uses, including stenting of the ureter, urethra, biliary tract, and the like. The present devices and methods will also be useful for the creation of temporary or long term lumens, such as the formation of fistulas. The controlled expansion prosthetic structures of the present invention will find their most immediate use as endovascular prostheses for the treatment of diseases of the vasculature, particularly aneurysms, stenoses, and the like. These prostheses will generally be radially expansible from a narrow-diameter configuration to facilitate introduction into the body lumen, typically during surgical cutdown or percutaneous introduction procedures. The present controlled expansion structures and materials will also find particular use as separate or integral sealing elements disposed at the ends of a prosthetic lumen or conduit to provide an atraumatic seal between the prosthesis and the body lumen.

Figure 1:
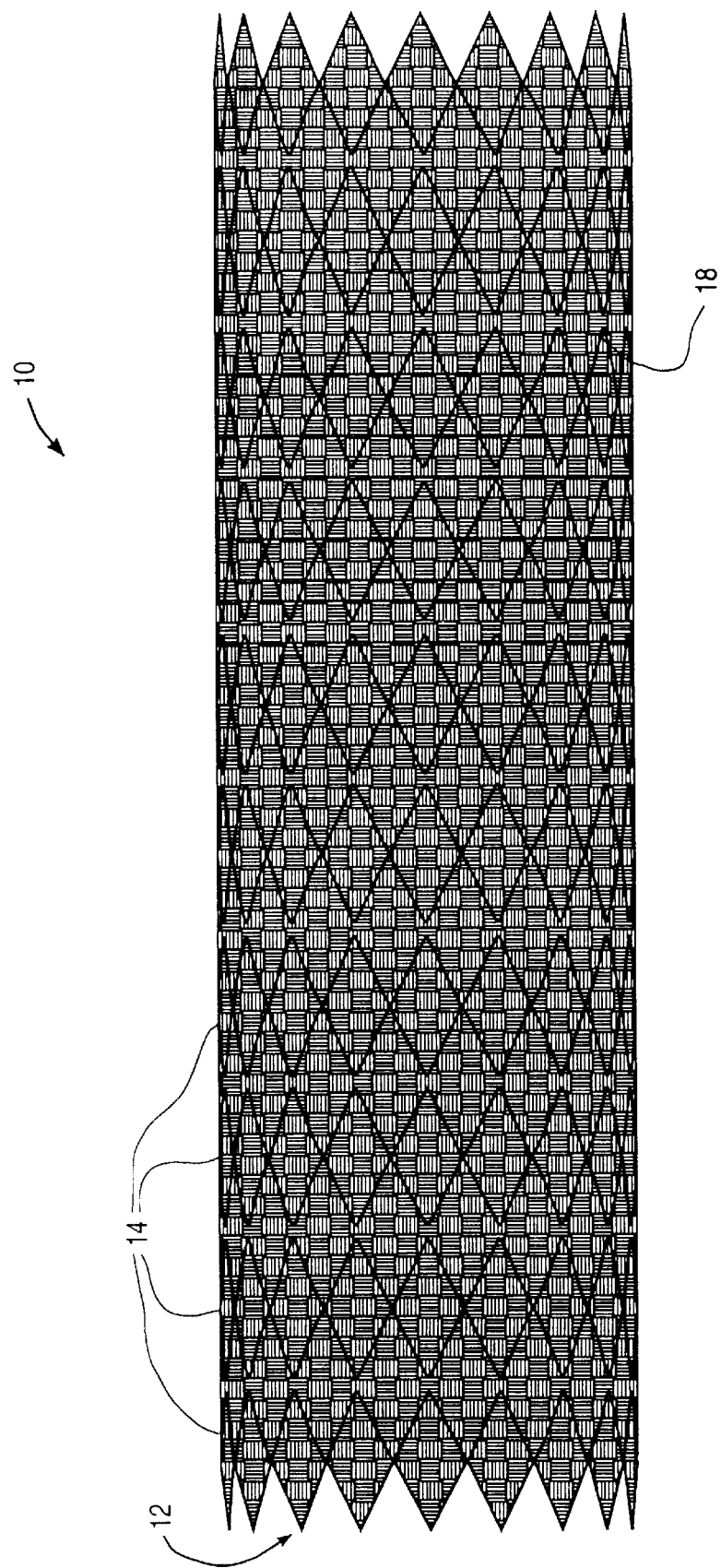
FIG. 1 is a side view of an exemplary vascular stent-graft having an expansible liner according to the principles of the present invention.

An exemplary cylindrical graft structure 10 is illustrated in FIG. 1. Prosthesis 10 comprises a perforate tubular frame 12 which here includes a plurality of independent (non-connected) ring frames 14. The tubular frame 12 supports an inner liner 18. Optionally, an outer liner is disposed over the ring frames, either instead of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other.

The prosthesis 10 will typically have a length in the range from about 20 mm to 500 mm, preferably from 50 mm to 200 mm, with a relaxed diameter in the range from about 4 mm to 45 mm, preferably being in the range from 5 mm to 38 mm. Alternative stint-graft structures, including advantageous modular prostheses which may be assembled in situ, are more fully described in U.S. patent application Ser. No. 08/538,706 (Attorney Docket No. 16380-38), the disclosure of which has previously been incorporated herein by reference.

Figure 2:
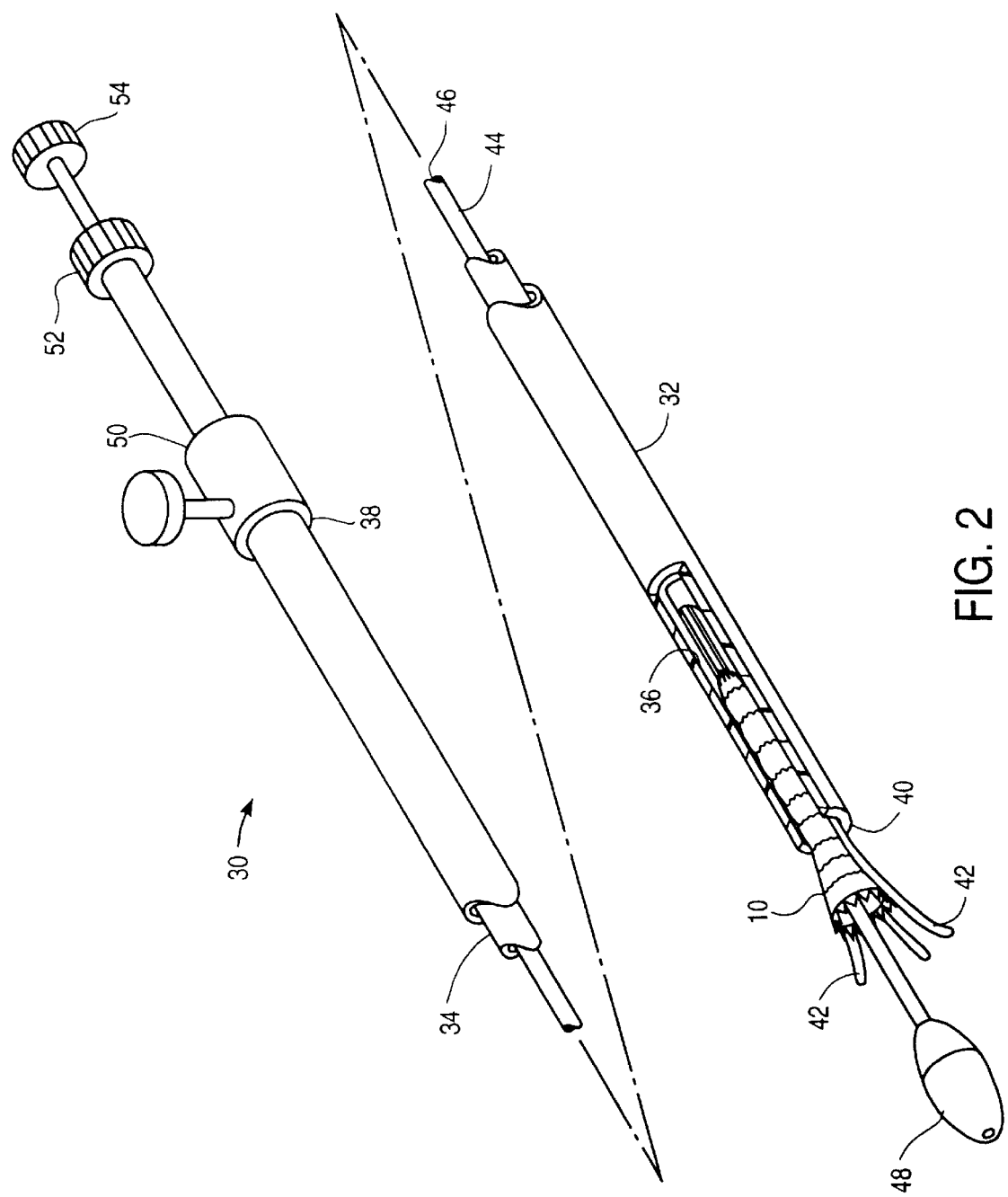
FIG. 2 is a perspective view of an exemplary delivery catheter for use with the prostheses of FIG. 1, with a portion of the distal end broken away to disclose a prosthesis therein.

Referring now to FIG. 2, an exemplary delivery catheter 30 for use with the endoluminal prostheses of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32.

A plurality of runners 42 extend distally from shaft 34. Runners 42 line a portion of the inner surface of lumen 36, and slide within the lumen with the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prosthesis 10 is radially compressed and restrained within the plurality of runners 42. In turn, cover 32 prevents runners 42 from expanding outward. Runners 42 are formed from a hard material, and distribute the expansion load of prosthesis 10 over the inner surface of central lumen 36. The deploying force is applied proximally against a slider 50 attached to distal end 38 of cover 30, while holding a luer fitting 52 at the distal end of shaft 34, thereby withdrawing the cover proximally from over the prosthesis. An additional luer adaptor 54 at the distal end of core shaft 44 allows the core shaft to be manipulated independently, and to be releasably secured to the shaft 34. Exemplary methods and devices for placement of the prostheses of the present invention are more fully described in co-pending U.S. patent application Ser. No. 08/475,200, the full disclosure of which is incorporated herein by reference.

Figure 3:
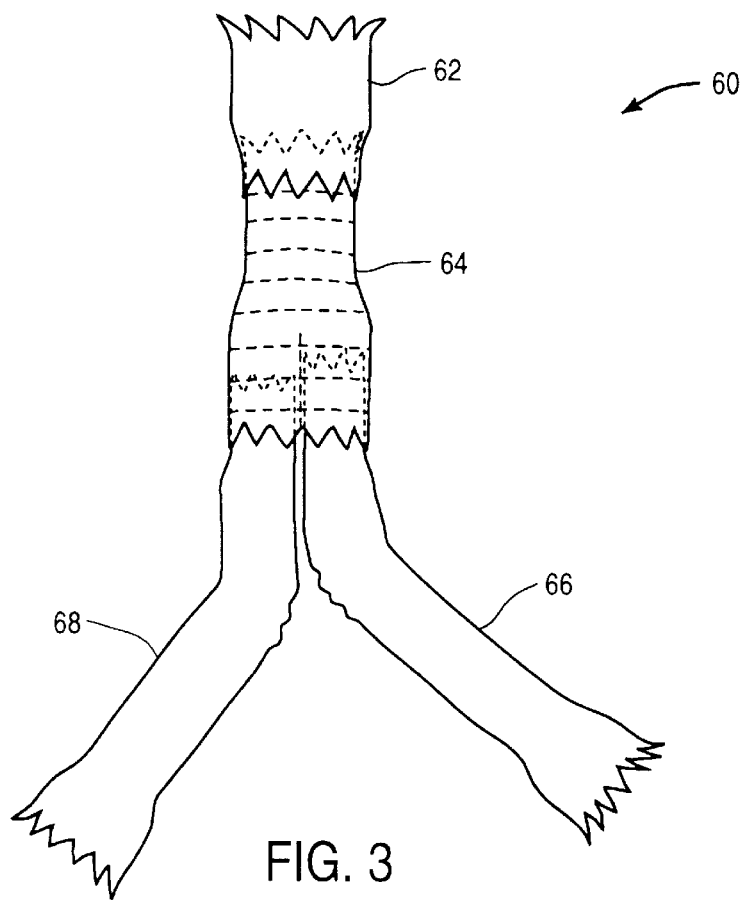
FIG. 3 illustrates a modular branching intraluminal prosthesis assembled from expansible prosthetic modules, according to the principles of the present invention.

Although the structures and methods of the present invention will generally be described with reference to simple tubular prostheses having a single lumen, it will be understood that the structures and methods of the present invention also encompass more complex branching and modular endoluminal prostheses. Referring to FIG. 3, for example, a branching endoluminal stent-graft 60 is assembled from prosthetic modules selected to match the needs of the diseased vascular system of the patient. A common lumen cuffed prosthetic module 62 seals and anchors the assembled prosthesis in the body lumen, typically within the abdominal aorta below the renal arteries and above the left and right iliac arteries. Y-connector module 64 engages cuffed common lumen module 62, and separates the blood flow for the iliac arteries. First angled branching prosthetic module 66 and second angled branching prosthetic module 68 engage the branch lumens of Y-connector module 64 to direct the luminal flow along first and second branching body lumens.

The modular construction and expansible structure of branching prosthesis 60 allows individual tailoring of the common lumen, first branch lumen, and second branch lumen to match the geometry of the body lumen system within predetermined limits. For example, a maximum perimeter of common lumen cuffed module 62 may be selected independently of the branching lumen perimeter limits. Modular bifurcated prostheses are more fully explained in co-pending U.S. Provisional Patent Application Ser. No. 60/008,254, the full disclosure of which is incorporated herein by reference. Additional sealing cuff structures and methods are described in co-pending U.S. patent application Ser. No. 08/525,989, the full disclosure of which is also incorporated herein by reference.

Figure 4:
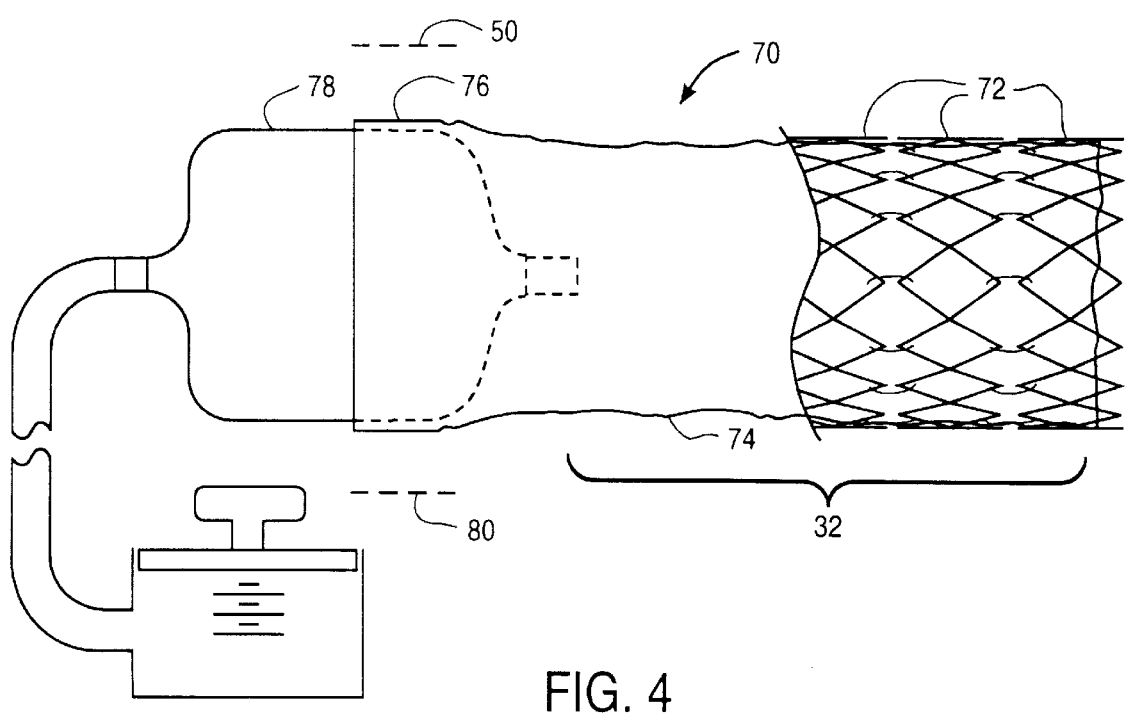
FIG. 4 is a schematic illustration of a method for selectively expanding an integral prosthetic sealing cuff, according to the principles of the present invention.

A method for expanding the prostheses of the present invention is schematically shown in FIG. 4. An expansible prosthesis 70 has frame rings 72 sutured to an expansible liner 74. Expansible liner 74 is formed from a material which expands plastically when subjected to a stress beyond a yield strength, and which remains expanded when the stress is removed, ideally exhibiting little or no spring back. By subjecting a cuff 76 to the expansive force of balloon 78, the liner perimeter at a selected cross-section is increased. Advantageously, the expansion of expansible prosthesis 70 may be performed prior to shipping the prosthesis as a production step, at the surgical site prior to introduction of the prosthesis within the patient body, or preferably, after deployment of tie prosthesis within a body lumen using an angioplasty-type balloon catheter or other minimally invasive expansion device.

Additional benefits can be realized by the application of radially expansive force from a balloon upon the liner of a deployed prosthesis. A balloon can be used to ensure full expansion of the liner from its compressed configuration, even when an inexpansible liner is supported by a self-expanding stent. The balloon may be inflated at one or more selected locations along the prosthesis, or may alternatively be sequentially applied along substantially the entire prosthetic lumen. Balloon expansion is particularly beneficial for smoothing wrinkles in the liner (or in the entire prosthesis), especially for ensuring that externally supported stent-grafts present a smooth prosthetic lumen in endovascular applications.

Frame rings 72 of expansible prosthesis 70 may comprise a material which is resilient, malleable, or some combination of the two. When resilient, frame rings 72 will preferably be radially restrained by expansible liner 74, even after expansion of the liner to the predetermined limit. Such a liner-restrained stent-graft structure avoids any loosening of the fabric after balloon 78 has been removed, as more fully described in application Ser. No. 08/538,706 (Attorney Docket No. 16380-003800), the disclosure of which has previously been incorporated herein by reference. It should be pointed out that while such taut structures (in which self-expansion of the frame was restrained by the liner) were referred to as "liner-limited" in that earlier application, they will here be called "liner-restrained" to avoid confusion with the prosthesis expansion limiting structures of the present invention.

The cuff 76 of expansible prosthesis 70 will expand to a predetermined limit, here shown as a maximum diameter 80.

The expansion or expansible prosthesis 70 is generally then limited by a structural element of the prosthesis itself. In particular, once expanded to maximum diameter 80, an element of either the liner 74 or the frame rings 72, or in some embodiments, the interface between the two, impedes further expansion.

Advantageously, some portion of expansible prosthesis 70 may include more conventional inexpansible liner materials, thereby ensuring that the prosthesis is not inadvertently expanded over a preselected region. In some embodiments, an inexpansible prosthesis conduit portion 82 prevents distention of the body lumen over much of its length, with sealing between the prosthetic lumen end and the surrounding body lumen provided by an integral expansible cuff 76. Alternatively, the expansible cuff could be formed as a separate structure or module, and assembled before deployment or in situ.

Frame Limited Expansion

Figure 5:
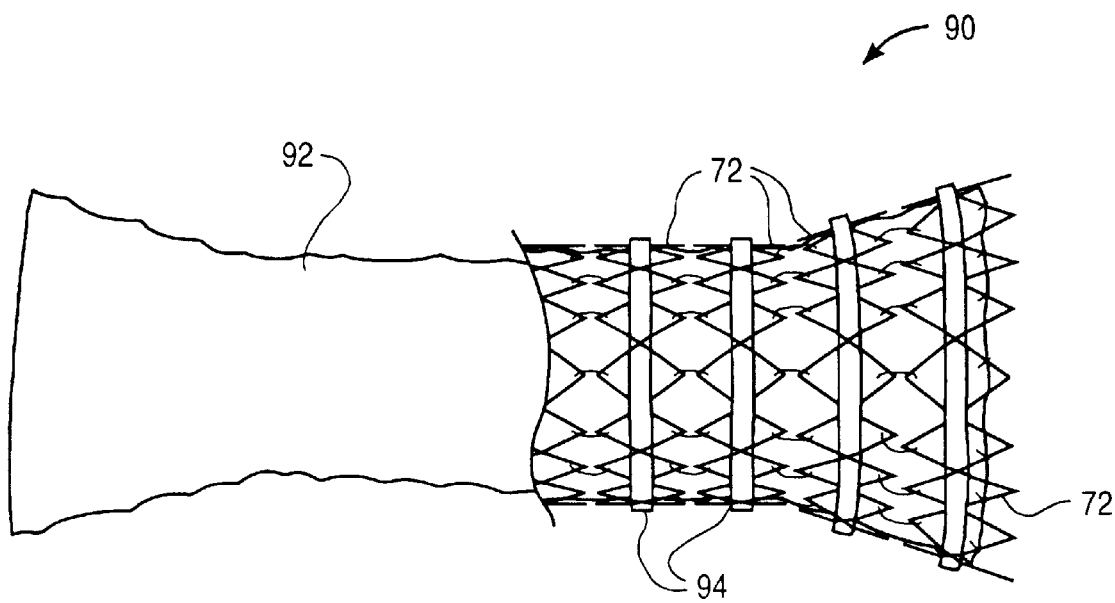
FIGS. 5 and 5A illustrate frame limited stent-grafts having circumferential belts which limit radial expansion, according to the principals of the present invention.

Referring now to FIG. 5, a frame belt limited stent-graft 90 includes an expansible liner 92 supported by a plurality of frame rings 72. A flexible frame belt 94 is woven through each ring frame, thereby reinforcing the frame against radial expansion when the frame perimeter is roughly equal to the circumference of the belt. Each frame belt is preferably flexible to facilitate radial compression of the prosthesis during positioning, and to adapt to expanded perimeters which are smaller than the expansion limit. Generally, the belts comprise a high strength inexpansible material so as to provide an ultimate expansion limit. Alternatively, the belts may be frangible or expansible, and thereby provide an intermediate limit, allowing still further expansion of the stent-graft.

Figure 5A:
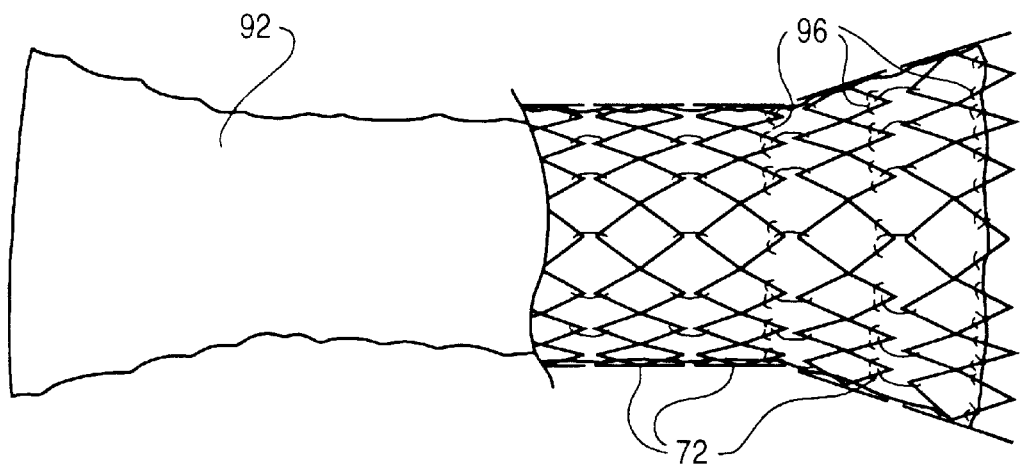

Frame belts 94 typically comprise medical tapes or belts which are woven through or wrapped around the perimeter of the frame, optionally being disposed only at selected axial regions of the prosthesis. In some embodiments, the frame belts may be formed as integral frame elements which straighten into circumferential bands when the frame is fully expanded. Alternatively, the frame belts may comprise circumferential loops of suture 96, as seen in FIG. 5A. Such suture belts may also be used to attach the frame to the liner, either as the sole means of attachment, or in combination with some additional attachment mechanism.

Figure 5C:
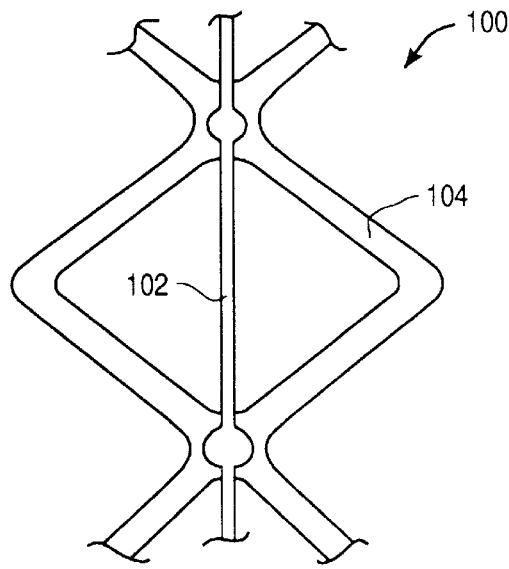
FIGS. 5B–E illustrate ring-frames having expansion limiting elements which releasably restrain expansion of the liner at a predetermined size.
Figure 5B:
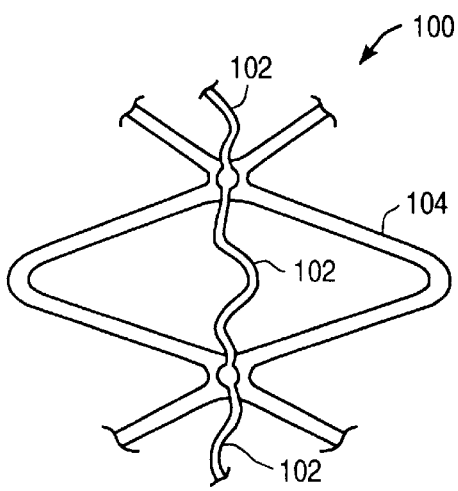
Figure 5D:
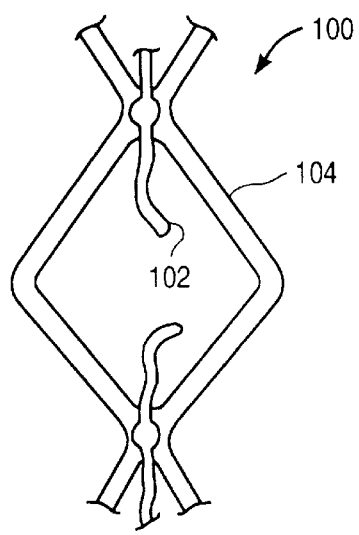

Referring now to FIGS. 5B–D, an alternative element for restraining expansion of the stent-graft comprises a reinforced perforate frame 100 having frangible perforation reinforcement elements 102. These flexible reinforcement elements straighten and support an associated perforation dimension, her; being the circumferentially oriented diagonal of diamond element 104. Such tensioned frangible elements generally comprises metal or polymer fibers which are adhesively bonded, welded, tied, riveted, integrally formed with, or otherwise attached to the frame. Perforation limiting elements might alternatively be used to limit the expansion angle of frame arms, or may take the form of compression members which restrict the axial diagonal of diamond element 104.

Figure 5E:
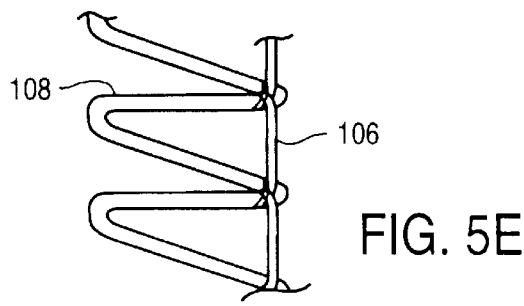

Reinforcement elements 102 fail in tension when the prosthesis is Under a predetermined expansion threshold load, thereby allowing overexpansion of the frame beyond the predetermined limit. Alternative expansible perforation reinforcement element 106, shown as fiber tied to a zig-zag frame ring 108 in FIG. 5E, comprises an expansible material such as partially oriented yarn, and thus allows gradual overexpansion Without leaving detached reinforcement element ends when an expansive load greater than a threshold load is applied.

Figure 6:
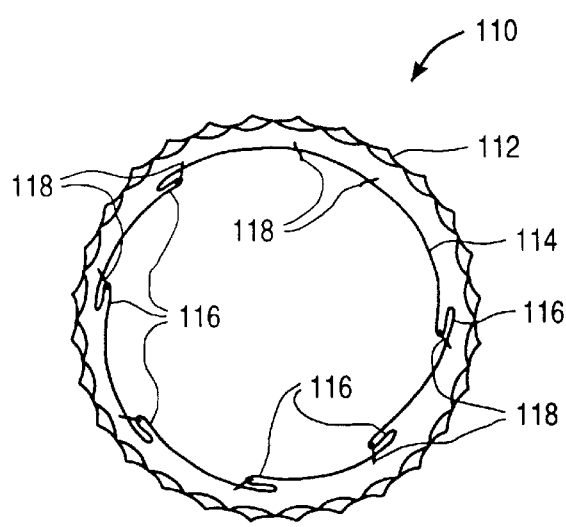
FIG. 6 is a cross-section of an endovascular stent-graft having an expansible liner wherein low strength attachments releasably maintain a plurality of axial folds.

Liners for frame limited prostheses are generally expansible to Latch the expanding frame, the liners typically comprising PTFE or partially oriented yarn. Alternatively, materials which are otherwise inexpansible may form expansible liners by including one or more folds in the fabric across the desired direction of expansion, as seen in FIG. 6. In other embodiments, the liner comprises an elastic tubular membrane, typically comprising spandex or urethane, which is held open by attachment to the expanded frame. Additional advantageous liner materials for frame limited expansion stent-grafts will also be described below regarding liner limited expansion.

Liner Limited Expansion

Referring now to FIG. 6, a first embodiment of liner controlled expansion stent-graft 110 includes a frame 112 and a folded liner 114 having a plurality of axially folds 116. These folds ark releasably maintained by frangible sutures 118, which separate and allow the diameter to increase incrementally. Alternatively, expansible sutures or attachments may provide gradual (rather than incremental) expansion of the liner. Advantageously, such a liner substantially retains its original porosity and strength when fully expanded.

Figure 7:
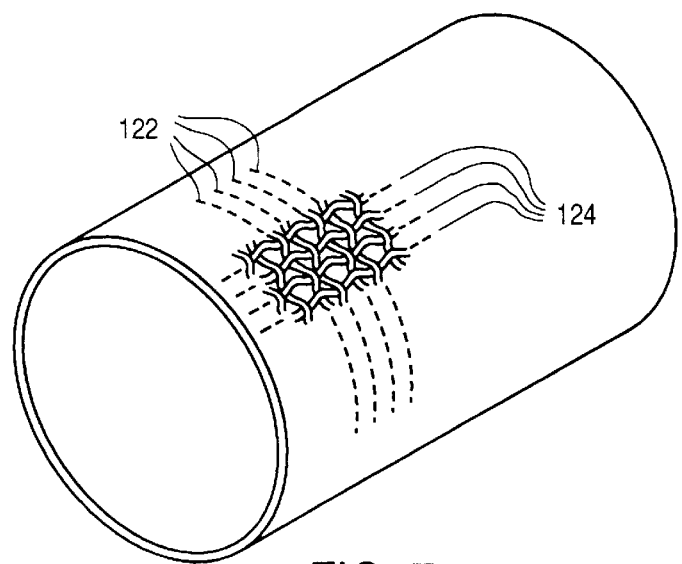
FIG. 7 is a perspective view of a radially expansible woven vascular graft having circumferentially oriented fibers which limit expansion, according to the principles of the present invention.

A tubular vascular graft 120 is shown in FIG. 7. As used herein, "graft" refers to structures which provide prosthetic lumens, both endoluminal structures and structures which are implanted through traditional invasive surgery. The term "liner" more narrowly refers to the prosthetic lumenal membrane of endoluminal structures.

Graft 120 comprises a continuously woven tube with fill fibers 122 in the circumferential direction and warp fibers 124 in the axial direction. Grafts may alternatively be knitted, braided, or sewn from flat sheet material, with woven grafts generally being preferred for endovascular applications because of their compressibility and dimensional stability.

Known endovascular grafts typically comprise fully drawn polyester warp and fill fibers, often comprising a woven polyester such as Dacron™. These woven fibers provide long lasting inexpansible liners which are biocompatible, and which also promote advantageous tissue ingrowth. However, such fully drawn warp fibers are not, by themselves, expansible in situ to match surrounding body lumen. The alternative use of partially oriented yarns in the radial direction is described in co-pending U.S. patent application Ser. No. 08/538,706 (Attorney Docket No. 16380-38), as previously incorporated herein by reference.

Fabric tubes woven from partially oriented yarns are extremely expansible, allowing prosthetic diameters to be increased by 80% or more. Unfortunately, expansion of much less than this amount (roughly 50% in test samples) results in an undesirable increase in porosity. Furthermore, as described above, fabrics woven with unreinforced partially oriented yarns may be susceptible to bulges or aneurysms of the prosthetic lumen during sizing or expansion. It should also be recognized that uneven expansion of such grafts by the balloon catheter or other expansion device could result in increased local porosity or open fistulas over a limited portion of the prosthetic lumen, even though the total perimeter of the graft has not been increased beyond the desired limit.

Sealing of the prosthesis against the surrounding vessel wall may also be compromised by such bulges. In particular, bulges in sealing cuffs (or otherwise adjacent to an end of the prosthesis) may result in folds that allow leakage around the prostheses, thereby maintaining pressure on the weakened portion of the vessel wall. For these reasons, graft 120 preferably includes alternative circumferentially oriented fibers which provide a limited amount of elongation.

Figure 8A:
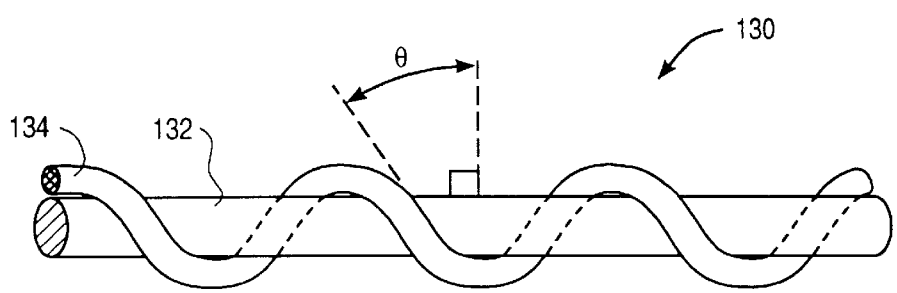
FIGS. 8A and B illustrate a composite yarn having inelastic fiber wrapped around a core fiber so that the inelastic fiber straightens and limits total elongation of the yarn, for use as a circumferentially oriented yarn in the graft of FIG. 7.
Figure 8B:
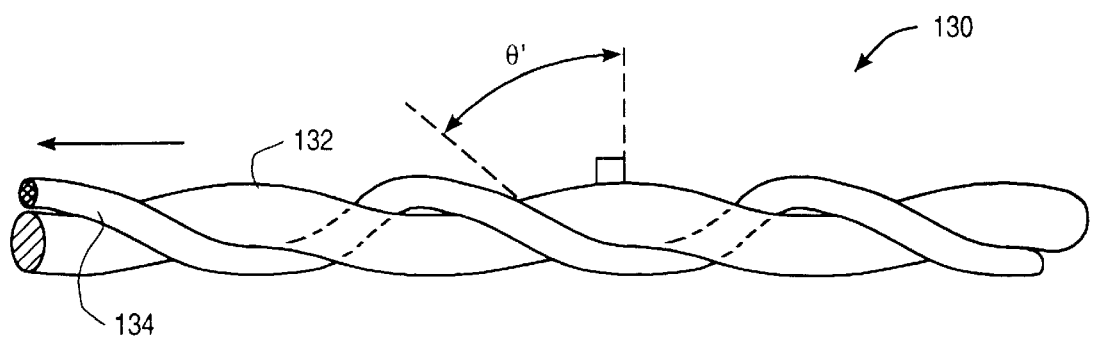

A particularly advantageous expansible composite fiber 130 for use in grafts will be described with reference to FIGS. 8A and B. Composite fiber 130 includes a core fiber 132 around which is wrapped an inexpansible fiber 134. When in a relaxed state, inexpansible fiber 134 assumes a serpentine shape, specifically being helically coiled about core fiber 132 with a pitch angle theta. It will be understood that the core fiber need not be entirely straight, but may also assume a serpentine shape when at rest. Regardless, wren the fiber is axially tensioned, as shown in FIG. 8B, the length of composite fiber 130 increases, even if inexpansible fiber 134 does not increase substantially in length. This elongation of the composite fiber results, at least in part, from a change in the helical shape of the inelastic coil.; In particular, the pitch angle of inexpansible fiber 134 increases to theta', and the helical diameter may also decrease, depending on the core fiber's characteristics.

Theoretically, the tensioned inexpansible fiber may eventually assure a linear shape, with the "core" fiber forced to assume a helical shape therearound. The actual elongation limit may occur substantially before that point, as the inelastic fiber will gradually absorb the tension load. It should also be understood that even an inexpansible fiber will generally increase somewhat under tension, and that even when "straightened" by tension, the composite fiber will still curve to follow the circumference of the graft, and may also bend according to the weave, knit, braid, or other circumferential fiber pattern. Nonetheless, the serpentine shape of inexpansible fiber 134 will become straighter as the graft is expanded.

Core fiber 132 may comprise any of a variety of alternative materials. Clearly, an expansible material, such as a partially Oriented fiber, will provide a controlled linear expansion of the composite fiber until any tensile load beyond the yield strength of the core is substantially transferred to the inelastic fiber. Where such an expansible core is desired, the core fiber preferably comprises polyester partially oriented fiber, ideally between 40 and 120 denier. The associated wrapped inelastic fiber will typically comprise fully drawn polyester between 10 and 80 denier.

Alteratively, composite fibers may include a core fiber 132 which has a preselected low ultimate tensile strength. Such a core fiber allows expansion of the composite fiber by failing at some threshold force, the core fiber generally failing intermittently along the composite fiber. The associated inexpansible element is then free to elongate, so that the total length of the composite fiber increases.

Still further alternative core fiber materials may be used within the scope of the present invention, including those materials described hereinbelow for use as the circumferential fibers in the graft of FIG. 7. For example, fibers comprising collagen or natural wool proteins may be used in the core, or a hydrogel having sufficient mechanical integrity when hydrated. Other monofilament cores may also be used. A core fiber comprising a temperature-sensitive polymer, would allow expansion with a heated balloon within the limit of the wrapped inelastic material. Preferably, the transition temperature is above body temperature so that such a heat sensitive polymer composite fiber is resistant to creeping when subjected to ordinary stresses at body temperatures. Hence, the composite fiber of the present invention encompasses a wide range of alternative materials.

Figure 9A:
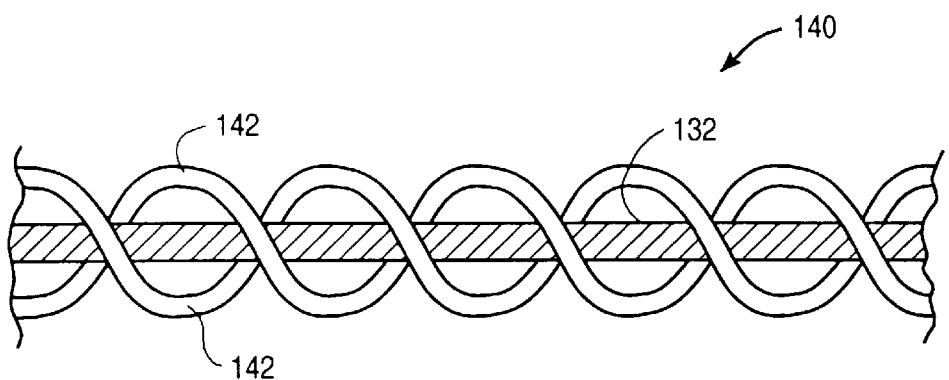
FIGS. 9A and B illustrate alternative wrapped composite yarn structures, for use as a circumferentially oriented yarn in the graft of FIG. 7.
Figure 9B:
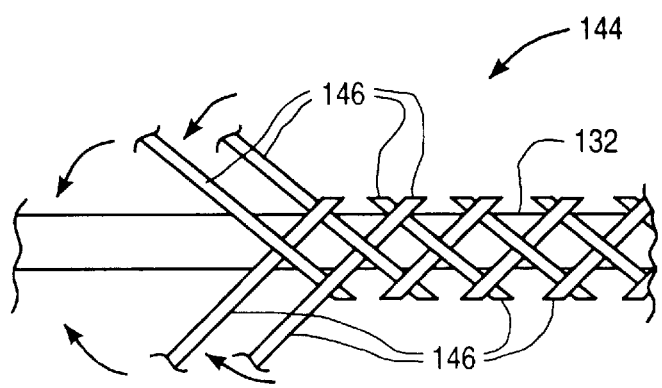

Alternative composite fiber wrap structures are shown in FIGS. 19A and B. A first alternative composite fiber 140 includes a plurality of inexpansible fibers 142 wrapped over core fiber 132 in the same direction. A second alternative composite fiber 144 has a plurality of inexpansible fibers 146 counterwound over the core. As seen in FIG. 9B, such counterwound fibers are optionally braided over the core, which will minimize changes to the core's path when tension is applied. A composite fiber having a core wrapped with two counterwound inelastic fibers would minimized the cost and complexity of preparing a counterwound composite fiber.

Figure 10:
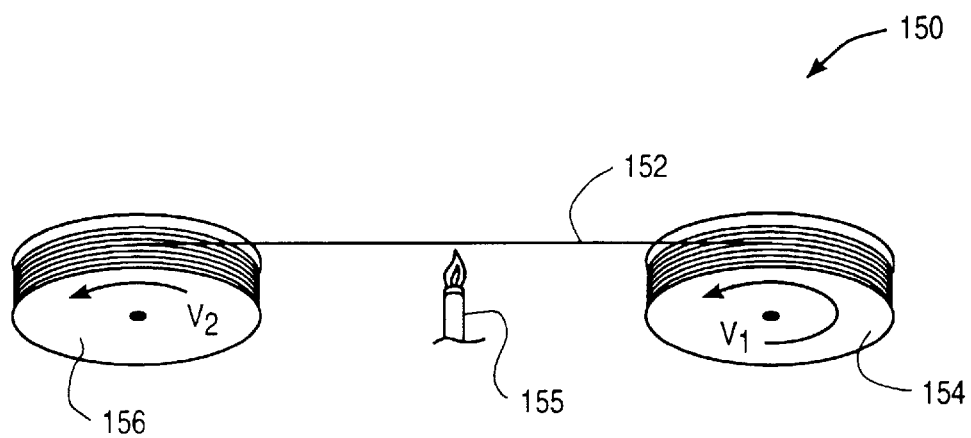
FIG. 10 illustrates a method for producing annealed fully drawn fibers, for use as a circumferentially oriented yarn in the graft of FIG. 7.

An alternative circumferential fiber which will provide controlled radial expansion of the graft of FIG. 7 comprises fully oriented yarns, typically of polyester, which have been annealed at less than melting temperature. The initial fully oriented yarn is widely available, being commonly used in knitting and weaving. The yarn is generally allowed to decrease in length during the annealing process, optionally by use of a collapsible cone, or by use of a reel system 150 as illustrated in FIG. 10.

Reel system 150 is similar to a drawing systems used to orient yarns. Fully oriented yarn 152 is supplied by a source reel 154 at a relatively high linear velocity V1. The yarn is heated (as represented by heating element 155), generally to a temperature of less than the melting point (250° C. to 260° C. for Dacron™), preferably to a temperature of about 150° C. to 260° C. The heated yarn is allowed to shrink, and is loaded on a take-up reel at a lower linear velocity V2.

With proper heat treatment temperatures, time, and shrinkage, grafts having annealed fully oriented yarns in the fill could provide controlled expansions of the prosthesis in the range from about 25 to 60 percent. The annealed fully oriented yarn begins to yield plastically at a substantially lower load level than the untreated fully oriented yarn. Once elongation begins, the yarn can be controllably elongated with increasing force. Advantageously, once the yarn is expanded within the structure of the graft, the properties of the yarn will gradually return to the properties of the pre-heat-treated fully oriented yarn. In fact, the maximum load at failure (in grams per denier) is similar to untreated fully oriented yarns, as long as the same base polymer is used in both.

A further alternative circumferential fiber which will provide controlled radial expansion of the graft of FIG. 7 comprises fully drawn yarns, typically of polyester, which have been texturized by twisting the yarns first in one direction, and then in the other, and by heat setting the yarn while it is twisted. A particularly advantageous texturizing process is sometimes referred to in the textile industry as "high crimp retention texturization," and is commercially available through Becker Industries. Yarns texturized with temperatures between about 200° C. and 220° C. and with spindle speeds of between about 4,200 and 4,400 RPM have produced linear elongations at break of between about 20 and 25%. The texturized yarn is preferably woven with minimum tension in the fill so that the texturized yarn would not be stretched during graft fabrication.

The texturized yarn produces a "crinkled" lumen surface, while the size of the lumen is generally smaller than would otherwise result from untreated fully oriented yarn. Upon balloon expansion, the diameter of the fabric increases to approximately the dimensions of an equivalent graft woven from fully oriented yarn. Hence, the texturized yarn in the fill provides an effective increase from the initial, unexpanded diameter. Once again, the material characteristics after expansion will be approximately equivalent to the original fully drawn yarns. Total effective expansions of up to about 20% should be available using such texturized yarns.

A still further alternative circumferential fiber which may provide controlled radial expansion of the graft of FIG. 7 comprises a temperature sensitive polymer such as a side-chain crystallizable copolymer, similar to those available fromiLandec Corp. of Menlo Park, Calif. under the trademark Intelimer®, or a radiation cross-link polymer.

Side-chain crystallizable polymers provide the ability to change state, between amorphous and crystalline, at a predetermined temperature. The transition temperature and physical properties of the material can be tailored, and the material is now being applied to medical products.

For use in the fill of the controlled expansion graft of the present invention, a fiber comprising a side-chain crystallizable polymer would preferably transition from expansible at body temperature to expansible when heated to somewhat above body temperature, i.e., about 43° C. To expand the graft in situ beyond the size allowed by the normally inexpansible sill fibers, a balloon would be inserted within the graft lumen and inflated with saline solution (or some other medium) which had been heated to a temperature slightly above the transition temperature. The balloon would warm the fill fibers and the side-chain crystallizable polymer to above the transition temperature, allowing the fill fibers to elongate. Expansion could then proceed from radial expansion force provided by increasing balloon pressure.

Advantageously, a prosthesis having such a temperature-sensitive graft may be introduced and positioned at the target site of a body lumen independently of the expansion balloon. A self-expanding stent-graft including a side-chain crystallizable polymer will preferably be compressible to a narrow diameter configuration, without any increase in delivery catheter diameter required to accommodate a concentric balloon. Alternatively, concentric prosthesis/expansion balloon delivery systems are also feasible.

Once the side-chain crystallizable polymer fill fibers were expended to conform the anatomy of the vessel, the balloon would We deflated so that the graft would again cool to body temperature, at which the fill fibers would resume their more crystalline state. Optionally, cooler saline solution could be infused in the balloon to reduce the graft temperature before deflation. The general properties and capabilities of side-chain crystallizable polymers were described in *Temperature Compensating Films for Produce*, Prepared Foods (September, 1992). As is generally true, the axial fibers may comprise more conventional graft materials, such as polyester or PTFE.

Radiation cross-link polymers behave very differently, generally shrinking when heated above a certain temperature. Advantageously, the reduced dimensions of these polymers may then be set by cooling. By forming oversized grafts having Circumferential fibers which comprise such radiation cross-linked polymers, preferably having a shrinkage temperature above body temperature, the graft cross-section could be controllably fitted by radially shrinking of the graft in situ over a heated balloon. Once again, infusion of cooler fluid will then set the prosthesis lumen size. Endoluminal prosthesis having such a shrink-to-fit graft structure will benefit from a high compressibility and flexibility to facilitate manipulation of the oversized graft within the body lumen prior to shrinking.

A still further alternative circumferential fiber which may provide controlled radial expansion of the graft of FIG. 7 comprises a hydrogel or other monofilament. Hydrogels are hydrophilic polymers that absorb water, thereby changing mechanical properties. Fibers comprising hydrogels would generally become softer and more extensible when placed in the aqueous environment of the body.

Hydrogels could be crosslinked or co-polymerized with hydrophobic monomers to maintain the desired mechanical integrity when hydrated. The intermolecular interactions of hydrogels can be broken, thereby allowing the hydrogels to change shape, by heating or by the action of certain organic solvents. Hence, fill fibers which comprise hydrogels may be controllably expanded. These properties of Hydrogels are more fully described in *Thermoplastic Hydrogels*, 23 British Polymer Journal, pages 257–259 (1990).

Still further alternative materials may provide fill fibers having the desired controlled radial expansion, including PTFE, Collagen, and natural wool proteins. PTFE is an expansible, biocompatible material which has an extensive history of use in the medical field. Similarly, collagen, which is available in a number of forms from Collagen Corp. of Palo Alto, Calilf., is a biocompatible material which has been used in medical applications.

Intearal and Separate Sealing Cuffs

Referring back to FIGS. 3 and 4, two particularly advantageous applications for expansible materials in endoluminal prostheses may generally be classified as integral sealing cuffs, such as cuff 76, and separate sealing cuffs, such as common lumen cuffed prosthetic module 62.

As described above, and as also described in co-pending U.S. Provisional patent application Ser. No. 60/008,254, and in U.S. patent application Ser. Nos. 08/525,989, and 08/525,989, all previously incorporated herein by reference, and in co-pending U.S. patent application Ser. No. 08/402,435, the full disclosure of which is herein incorporated by reference, the selective plastic expansion of one or more ends of the prosthesis promotes sealing between the prosthesis and the surrounding body lumen without distending the body lumen along the entire prosthetic lumen. Advantageously, prostheses having such sealing cuffs thereby provide therapy for an aneurysm which minimizes stress on the weakened portion of the vessel wall. Integral and separate sealing cuffs which include the expansion limiting structures described above will further help to limit the distention of the healthy portion of the body lumen against which the prosthesis is sealed.

Integral sealing cuffs are often formed as an extension of the prosthetic liner, optionally by a simple change in the fill material of the liner, the structure otherwise being consistent with the body of the prosthesis. A particularly advantageous integrated sealing cuff may be formed by switching from an inexpansible fully drawn fill material to a partially oriented yarn adjacent the end of the liner.

Alternatively, the cuff may have a structure which produces very different expansion characteristics than the remaining body of the prosthesis. Much of expansible prosthesis 70, for example, comprises inexpansible prosthesis conduit portion 82. Within a weakened blood vessel, this conduit provides a flow path for the blood. While this conduit preferably flexes with the body lumen, the axial length of conduit portion 82 will preferably substantially remain constant, particularly while the prosthesis increases in cross-section during deployment (or any size adjustment) to ensure that the conduit extends beyond the diseased portion of the body lumen. On the other hand, the sealing cuff serves primarily to seal between the conduit and the surrounding body lumen, and optionally to help anchor the prosthesis. Hence, changes in the axial length of the sealing cuff are of less concern.

Figure 11B:
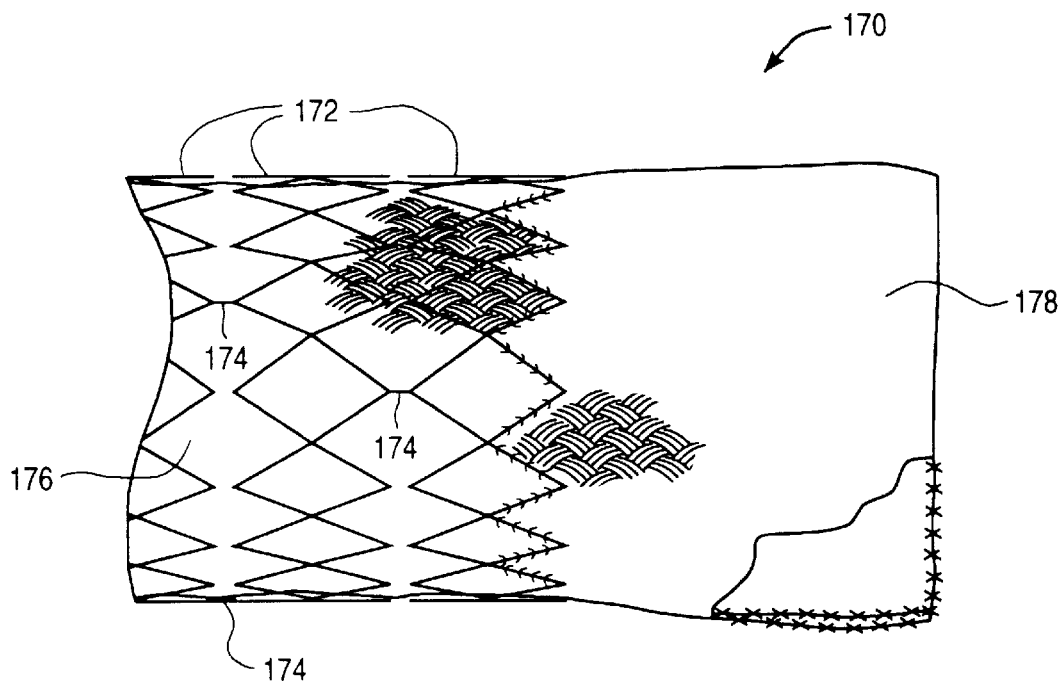
FIGS. 11A and 11B illustrate alternative integral sealing cuffs having a braided sealing structure, according to the principals of the present invention.
Figure 11A:
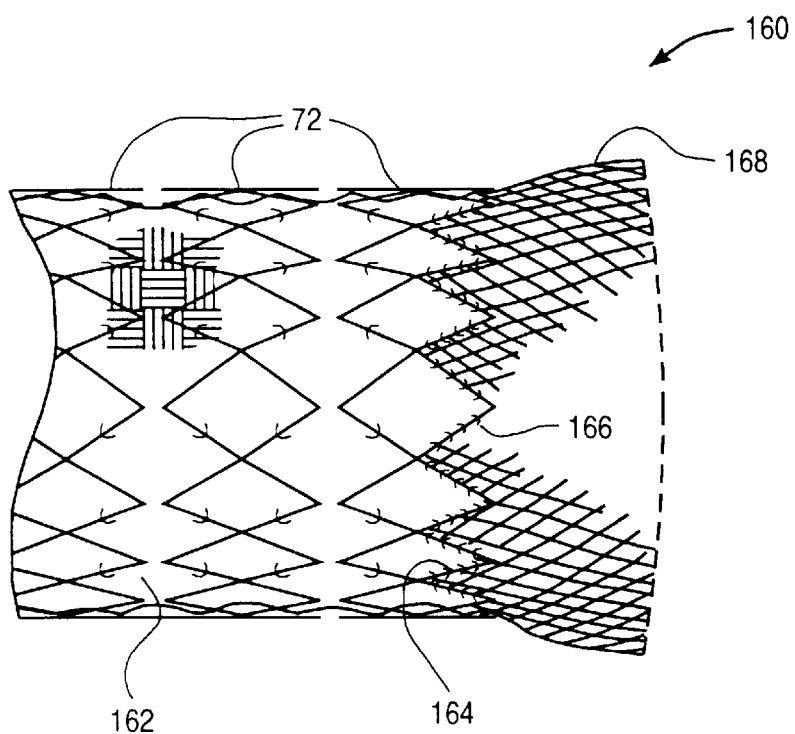

Referring now to FIG. 11A, an integral braided cuff prosthesis 160 comprises a plurality of independent ring frames supporting a conventional liner 162. An axial end 164 of the liner is stitched to the adjacent ring frame with a crown stitch pattern 166, which also attaches a braided cuff 168. Alternatively, the braid may be stitched along the midline of the adjacent frame ring and extend equidistant inward along liner 162. Braided materials are highly radially expansible, but are not often used for prosthetic conduits as radial expansion generally also results in a reduction in length of the prosthetic lumen. However, as this coupling of the radial and axial dimensions does not impeded the sealing of the end of the prosthesis, braided cuff 168 is free to shorten as required. In fact, the cuff may alternatively be oriented back along the prosthesis.

Referring now to FIG. 11B, an alternative integral braided cuff prosthesis 170 comprises interconnected ring frames 172 having joints 174 which maintain the axial length of the prosthetic conduit during radial expansion. The liner 176 comprises braided material which extends axially beyond the frame to also form a folded cuff 178. The braided material is folded outward and extends back to the frame, where it is attached by crown stitching. Hence, as the prosthesis expands radially, the length of the cuff decreases, but the length of the prosthetic conduit is not changed. Optionally, expansion of the frame may be limited as described above.

Separate sealing cuffs may make use of similar structures, often having a structure which limits a cross-section of the cuff along an interface with the remainder of the prosthesis. Use of such an inexpansible interface in common lumen cuffed prosthetic module 62 (FIG. 3) facilitates safe expansion of Y-connector module 64 therein during assembly. Alternatively, a separate sealing cuff which extends axially from within an inexpansible prosthesis may rely on that other prosthesis to limit expansion.

Figure 12:
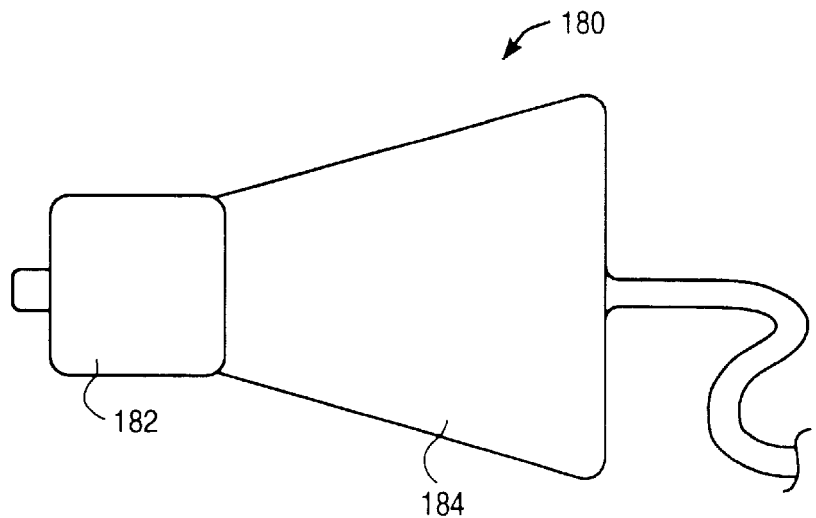
FIGS. 12—13 illustrate balloon catheters having a plurality of chambers and methods for their use to grip and selectively expand an integral sealing cuff of an endoluminal prosthesis.
Figure 12A:
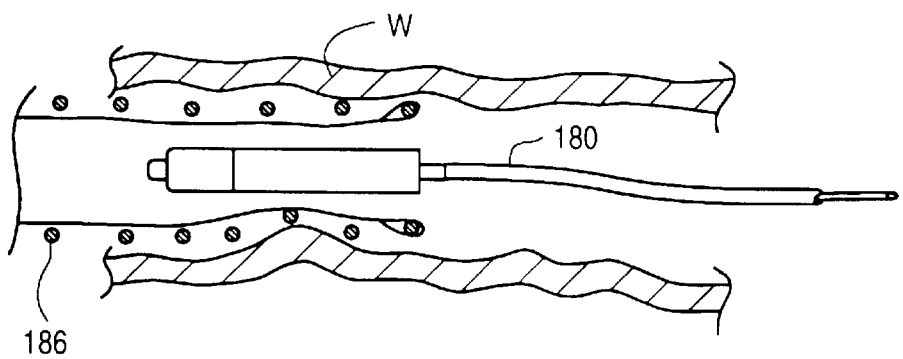
Figure 12B:
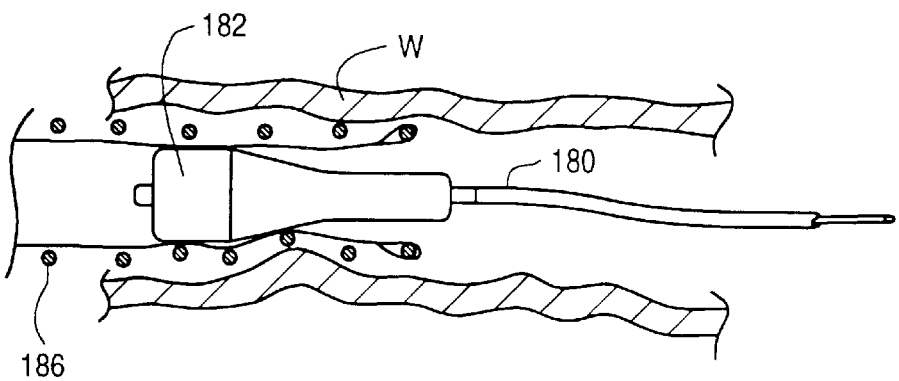
Figure 12C:
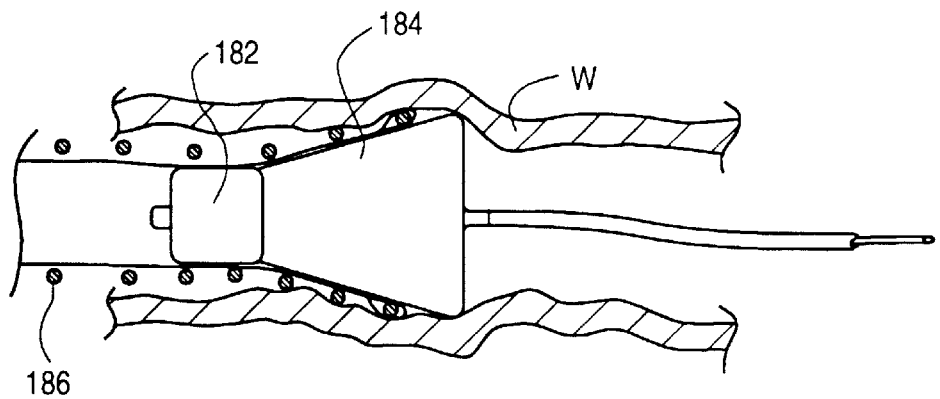
Figure 12D:
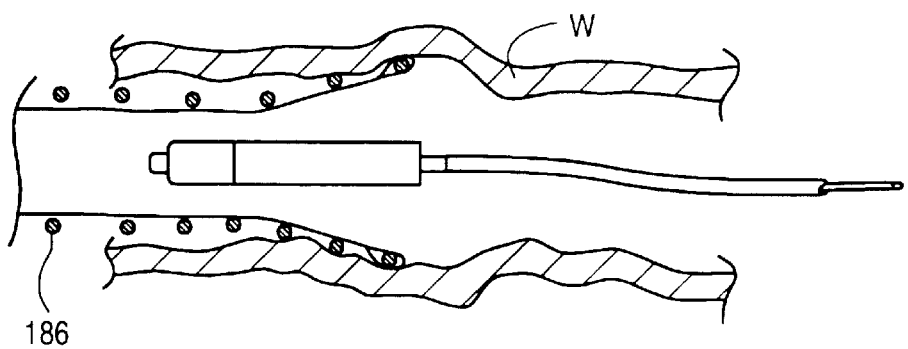
Figure 13:
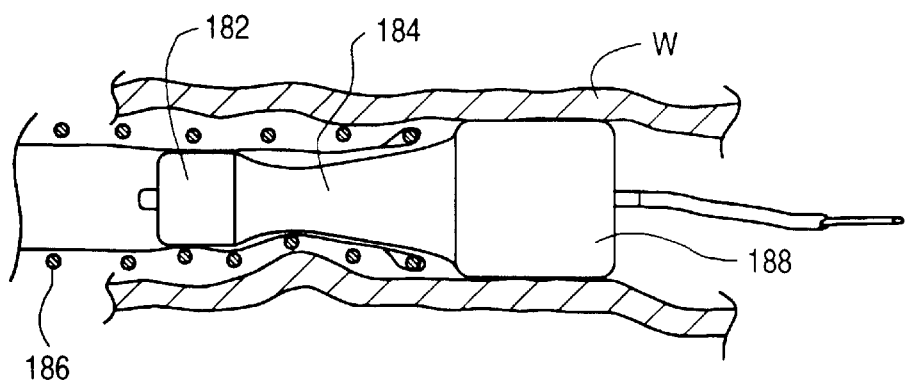

Referring now to FIGS. 12–13, an advantageous balloon catheter 180 facilitates selective expansion of an integral or separate sealing cuff within a body lumen without the prosthesis sliding off the end of the balloon. Balloon catheter 180 comprises a prosthesis gripping chamber 182 and an expansion chamber 184. The balloon is inserted into a body lumen and positioned within a prosthesis 186. Prosthesis gripping chamber 182 is first inflated, optionally along an inexpansible portion of the prosthesis, to firmly engage the prosthesis ant prevent relative movement between the prosthesis and balloon.

The expansion chamber 184 is then inflated to expand the end of prosthesis 186 to the desired cross section, after which both chambers can be deflated and the balloon removed. Optionally, a vessel wall gripping chamber 188 may be inflated prior to expansion with the expansion chamber, thereby securing the position of prosthesis and balloon with respect to vessel wall W, as can be seen in FIG. 13. The vessel wall gripping balloon is preferably expandable using sufficiently low pressures to avoid injury to the vessel while engaged.

While the foregoing has been described in some detail, for purposes of clarity and understanding, certain changes and modifications will be obvious to those of skill in the art. Thus the scope of the present invention is limited only by the appended claims.

What is claimed is:

1. A limited expansion graft comprising a fabric including composite yarns having serpentine inexpansible fiber and expansible fiber so that the inexpansible fiber straightens during expansion of the graft to prevent expansion of the fabric beyond a predetermined limit.

2. A graft fabric as claimed in claim 1, wherein the fabric forms a tube, and wherein the composite yarns are substantially circumferentially oriented.

3. A graft fabric as claimed in claim 1, wherein the inexpansible fiber comprises fully drawn polyester.

4. A graft fabric as claimed in claim 3, wherein the expansible fiber comprises a partially oriented polyester over which the fully drawn polyester is wound.

5. An expansible graft comprising a fabric tube which defines an axial direction and a circumferential direction, the fabric tube including fully oriented polyester yarn oriented in the circumferential direction, wherein the fully oriented polyester yarn has been heat treated to facilitate in situ expansion of the graft.

6. An expansible graft as claimed in claim 5, wherein the fabric comprises a woven material, and wherein the heat treated yarn has been annealed at a temperature between about 150° C. and 260° C.

7. An expansible graft as claimed in claim 5, wherein the graft is expansible by an amount in the range between 25% and 60%.

8. An expansible graft comprising a fabric tube which defines an axial direction and a circumferential direction, the fabric tube including fully oriented polyester yarn oriented in the circumferential direction, wherein the fully oriented polyester yarn has been texturized by twisting the yarn and heat setting the twisted yarn to promote in situ expansion of the graft.

9. An expansible graft as claimed in claim 8, wherein the graft is expansible by up to 20%.

* * * * *